United States Patent
Ryan et al.

(10) Patent No.: US 6,740,836 B2
(45) Date of Patent: May 25, 2004

(54) SYSTEM AND METHOD FOR OUTSORTING SUSPECT MAIL FROM AN INCOMING MAIL STREAM

(75) Inventors: William E. Ryan, Monroe, CT (US); Mark Cullen, Bethany, CT (US); Robert K. Gottlieb, Milford, CT (US); Joseph D. Mallozzi, Trumbull, CT (US); Alberta A. Vitale, East Haven, CT (US)

(73) Assignee: Pitney Bowes Inc., Stamford, CT (US)

( * ) Notice: Subject to any disclaimer, the term of this patent is extended or adjusted under 35 U.S.C. 154(b) by 169 days.

(21) Appl. No.: 10/035,541

(22) Filed: Dec. 31, 2001

(65) Prior Publication Data

US 2003/0125835 A1 Jul. 3, 2003

(51) Int. Cl.[7] .................................................. B07C 5/00
(52) U.S. Cl. ...................................... 209/584; 700/223
(58) Field of Search ............................. 209/589, 584, 209/576, 577; 700/223; 271/2

(56) References Cited

U.S. PATENT DOCUMENTS

| | | | |
|---|---|---|---|
| 4,485,308 A | 11/1984 | Rabatin | 250/461.1 |
| 4,831,555 A | 5/1989 | Sansone et al. | 364/519 |
| 5,166,755 A | 11/1992 | Gat | 356/419 |
| 5,600,303 A | 2/1997 | Husseiny et al. | 340/568 |
| 5,675,070 A | 10/1997 | Gelperin | 73/23.34 |
| 5,971,391 A | 10/1999 | Salomon et al. | 271/153 |
| 6,003,857 A | 12/1999 | Salomon et al. | 271/122 |
| 6,135,441 A | 10/2000 | Belec et al. | 271/35 |
| 6,161,830 A | 12/2000 | Yap | 271/181 |
| 6,169,936 B1 | 1/2001 | Lohmann | 700/224 |
| 6,217,020 B1 | 4/2001 | Supron et al. | 271/149 |
| 6,303,889 B1 | 10/2001 | Hayduchok et al. | 209/584 |
| 6,328,300 B1 | 12/2001 | Stefan et al. | 271/2 |
| 6,567,008 B1 | 5/2003 | Sansone | 340/666 |
| 2002/0124664 A1 | 9/2002 | Call et al. | 73/863.22 |
| 2002/0126008 A1 | 9/2002 | Lopez et al. | 340/540 |
| 2002/0141613 A1 | 10/2002 | Sansone | 382/101 |
| 2003/0058099 A1 | 3/2003 | Lopez et al. | 340/540 |
| 2003/0145664 A1 * | 8/2003 | Schwarz et al. | 73/863.22 |

FOREIGN PATENT DOCUMENTS

EP     0 298 769 A2    8/1988    ............. B07C/1/00

* cited by examiner

*Primary Examiner*—Kenneth W. Noland
(74) *Attorney, Agent, or Firm*—Alberta A. Vitale; Angelo N. Chaclas; George M. Macdonald

(57) ABSTRACT

An embodiment of the system of the present invention generally comprises a mailpiece sorting apparatus which includes a feeder, an OCR scanner, a video scanner, a mailpiece transporter, a diverter and output module, compartments or bins for receiving sorted mailpieces, optical character recognition system for reading addressee information, an addressee database, a suspect database, and microprocessor based control system. In alternate embodiments of the present invention: the system is contained in a detection area and clean room and/or connection to an investigation entity. The system and method of integrates prediction of the presence of life harming material in mailpieces with mailpiece processing so as to help deter delays in incoming mail delivery caused by the presence of life harming material the suspected presence of life harming material and to protect the intended recipients from harm.

17 Claims, 13 Drawing Sheets

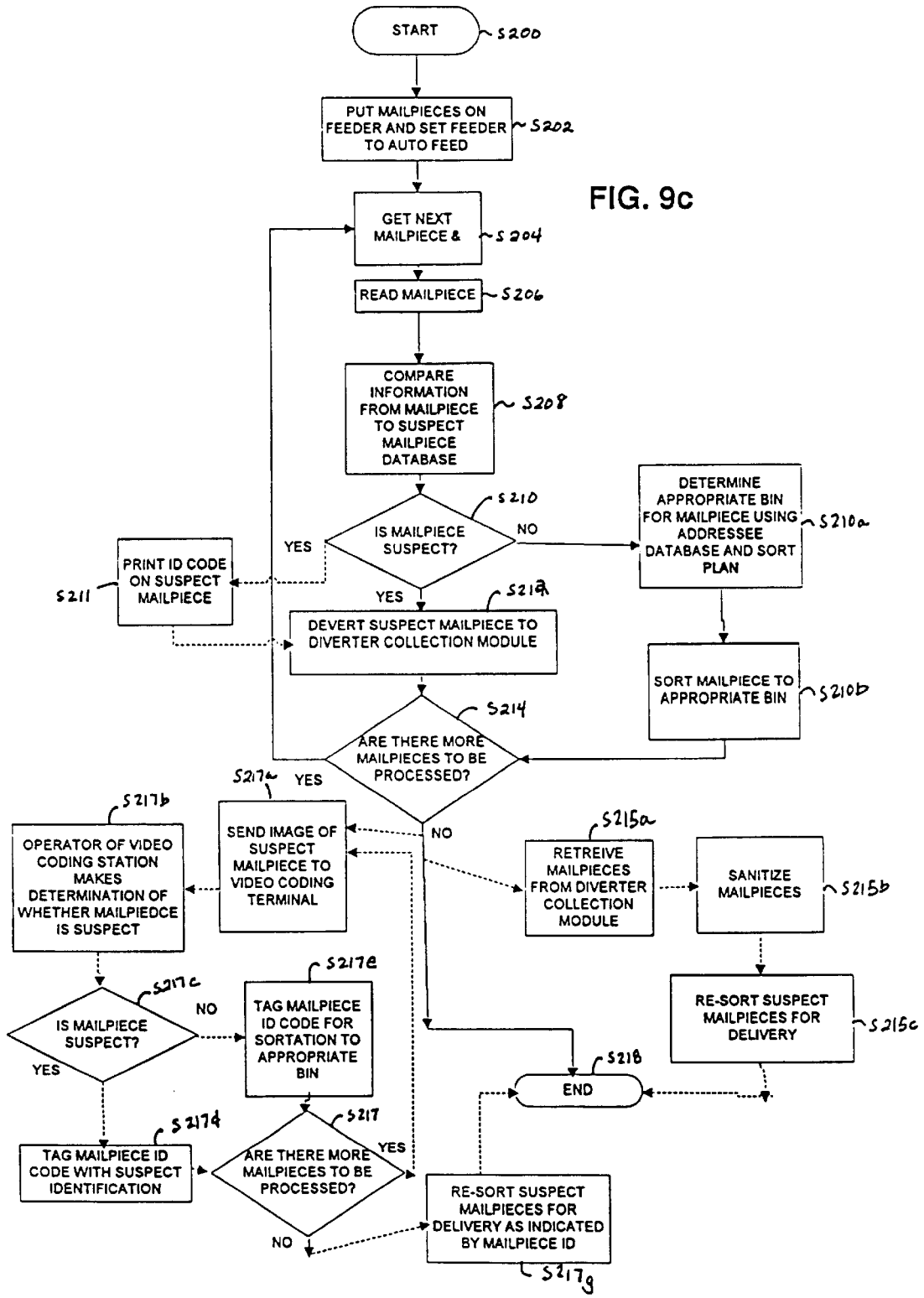

SYSTEM AND METHOD FOR OUTSORTING SUSPECT MAIL FROM AN INCOMING MAIL STREAM

CROSS REFERENCE TO RELATED APPLICATIONS

Reference is made to commonly assigned: co-pending patent applications: Ser. No. 10/036,982 filed herewith titled SYSTEM FOR DETECTING THE PRESENCE OF HARMFUL MATERIALS IN AN INCOMING MAIL STREAM in the name of William Ryan et al.; Ser. No. 10/036,991 filed herewith titled SYSTEM FOR SANITIZING INCOMING MAIL in the name of William Ryan et al.; and Ser. No. 10/035,546 filed herewith titled SYSTEM FOR SANITIZING AND SORTING MAIL in the name of William Ryan et al.

FIELD OF THE INVENTION

The invention disclosed herein relates generally to automated mail sorting and more particularly, a system and method that predicts the presence of life harming materials in mailpieces.

BACKGROUND OF THE INVENTION

The processing and handling of mailpieces consumes an enormous amount of human and financial resources, particularly if the processing of the mailpieces is done manually. The processing and handling of mailpieces not only takes place at the Postal Service, but also occurs at each and every business or other site where communication via the mail delivery system is utilized. That is, various pieces of mail generated by a plurality of departments and individuals within a company need to be addressed., collected, sorted and franked as part of the outgoing mail process. Additionally, incoming mail needs to be collected and sorted efficiently to ensure that it gets to the addressee (i.e. employee or department) in a minimal amount of time. Since much of the documentation and information being conveyed through the mail system is critical in nature relative to the success of a business, it is imperative that the processing and handling of both the incoming and outgoing mailpieces be done efficiently and reliably so as not to negatively impact the functioning of the business.

Various services are used in the United States and other countries for delivery of mail (incoming mail) to individuals and businesses to recipients to whom the sender does not want to deliver personally. These services include, for example, the United States Postal Service (USPS) and other courier services, e.g., Federal Express®, Airborne®, United Parcel Service,® DHL®, etc., hereinafter called "carriers". Unfortunately, sometimes the delivered materials may be illegal and/or hazardous to the health of the recipient and to the party who is delivering the goods, e.g., life-harming. Examples of life-harming materials are explosives; gun powder; blasting material; bombs; detonators; smokeless powder; radioactive materials; ammunition; atomic weapons; chemical compounds or any mechanical mixture containing any oxidizing and combustible units, or other ingredients in such proportions, quantities, or packing that ignite by fire, friction, concussion, percussion or detonation of any part thereof which may and is intended to cause an explosion; poisons; carcinogenic materials; caustic chemicals; hallucinogenic substances; illegal materials; drugs that are illegal to sell and/or dispense; and substances which, because of their toxicity, magnification or concentration within biological chains, present a threat to biological life when exposed to the environment, etc.

Soon after the Sep. 11, 2001, terrorist attack on the United States, someone and/or a group of people, has been adding harmful biological agents to the mail. The addition of harmful biological agents to the mail submitted to the USPS has caused the death of some people and necessitated the closure of some post offices and other government office buildings and has caused delays in the sortation and delivery of mail including the delivery of incoming mail to businesses. Individuals who receive and handle mail are encouraged to use safety precautions such as: washing their hands thoroughly with soap and water after handling mailpieces; avoiding shaking mailpieces; avoiding bumping or sniffing mailpieces; and avoiding handling of mailpieces suspected of contamination. These measures can be impractical when the volume of mail such as the incoming mail at a business is large. Thus, there is an urgent need to exclude or detect life-harming materials that are included in the mail in such a way that the delivery of the mail is efficient, reliable and safe and thus does not to negatively impact the functioning of the business.

Various automated mail handling machines have been developed for processing incoming mail (removing individual pieces of mail from a stack and performing subsequent actions on each individual piece of mail). Generally, the mail handling machines separate individual mailpieces from a stack, read the mailpieces using an optical character recognition (OCR) system and compare the read information to an addressee database in order to determine the appropriate destination points for delivery of the mailpieces. Previously, if a determination could not be made by the incoming mail handling machine as to the addressee, a video image of the mailpiece was viewed by an operator and in the case where the addressee image was readable by the operator, addressee information was keyed into the system and associated with an identification number for the mailpiece. The previously rejected mailpieces are then resorted by reading the identification information which can be printed on the mail during the first sort. The identification information is linked with the addressee information manually keyed in by the operator during the reject processing/video coding sequence and is used to sort the mailpiece to the proper destination bin. Video processing of mailpieces has been performed at on-site video coding terminals or off-site video coding facilities where the video image is transmitted for determination of addressee by an operator. The information is then transferred back to the sorting apparatus. These automated mail sorting apparatus do not contain the ability to detect and/or sanitize mailpieces suspected of containing life harming agents.

Thus, there is an urgent need to exclude or detect life-harming materials that are included in the mail in such a way that the delivery of the mail is efficient, reliable and safe and thus does not negatively impact the functioning of the business. Thus one of the problems of the prior art is that a system is not available for processing incoming mail and detecting and/or sanitizing mailpieces suspected of containing life harming agents. Therefore, a system and method of processing incoming mail is needed which integrates, prediction of harmful content, detection and/or sanitization with the mailpiece processing so as to help deter delays in incoming mail delivery caused by the presence or suspected presence of life harming material and/or to detect and/or sanitize the mail so as to protect the intended recipients from harm.

SUMMARY OF THE INVENTION

This invention overcomes the disadvantages of the prior art by providing a system and method for processing incoming mail which integrates prediction of suspect status of the mailpiece so as to help deter delays in incoming mail delivery caused by the presence of life harming material and to protect the intended recipients from harm. This in turn affords for less delays in mailpiece processing.

The present invention is directed, in general to automated mailpiece sorting apparatus and more particularly, a system for predicting the presence of harmful materials in a mailpiece. The system generally comprises a mailpiece sorting apparatus which includes a feeder, an optical character recognition (OCR) scanner, a video scanner, a mailpiece transporter, a diverter and output module (or an integrated diverter/stacker module), compartments or bins for receiving sorted mailpieces, an OCR system for reading addressee information, an addressee database, a suspect database, a personal computer (PC) or microprocessor based control system. The mailpiece sorting apparatus of the present invention also comprises a suspect database containing criteria for suspect mailpieces.

In an embodiment of the present invention suspect mailpieces are determined by reading the mailpieces and using a pre-set criteria to make the suspect determination; suspect mailpieces are diverted from the mail stream. Once the first pass sorting is completed, the suspect mail may be further processed using video coding to make a subsequent determination of suspect status. In another embodiment of the present invention the system is contained in a detection area and clean room. In another embodiment of the present invention the system is connected to an investigation entity which compiles information regarding suspect mailpieces.

An advantage of the method of the present invention is that it provides a system and method for helping to deter delays in the mail delivery. Another additional advantage of the present invention is that the negative impact of delayed mail delivery is reduced. Other advantages of the invention will in part be obvious and will in part be apparent from the specification. The aforementioned advantages are illustrative of the advantages of the various embodiments of the present invention.

DESCRIPTION OF THE DRAWINGS

The above and other objects and advantages of the present invention will be apparent upon consideration of the following detailed description, taken in conjunction with accompanying drawings, in which like reference characters refer to like parts throughout, and in which.

FIG. 9c illustrates an embodiment of the method of the present invention for detecting or predicting suspect mailpieces in a mail stream and diverting such mailpieces from delivery.

DETAILED DESCRIPTION OF THE PRESENT INVENTION

Figure 1A:
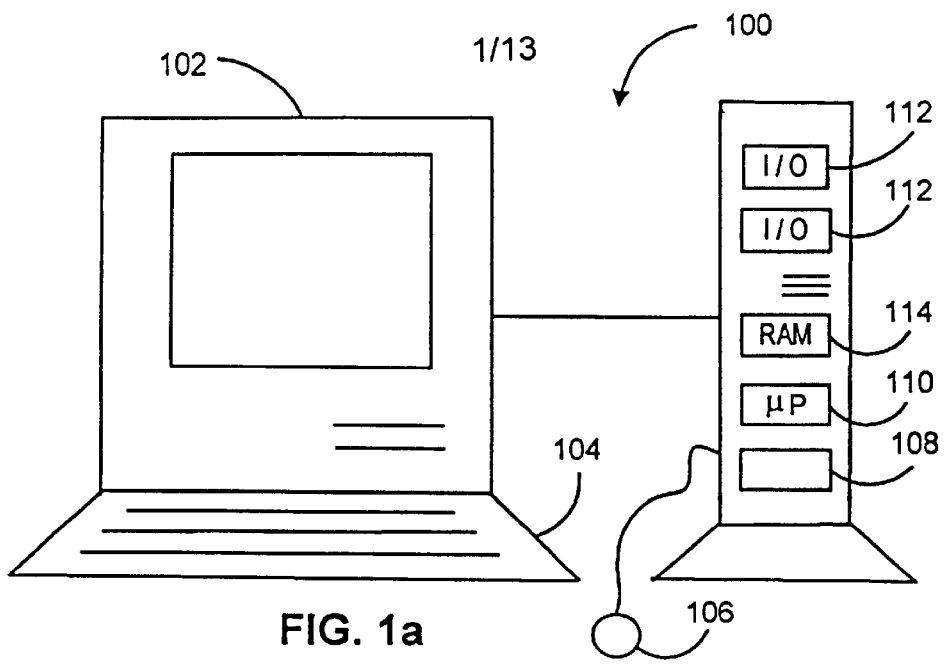
FIG. 1a is a block diagram that illustrates a computer system with which an embodiment of the invention may be implemented or controlled.

In describing the present invention, reference will be made herein to FIGS. 1–9 of the drawings in which like numerals refer to like features of the invention. Features of the invention are not necessarily shown to scale in the drawings.

Automated Mailpiece Sorting Apparatus Overview

FIG. 1a is a block diagram that illustrates a computer system 100 with which an embodiment of the invention may be implemented. Computer system 100 may be a personal computer which is used generically and refers to present and future microprocessing systems with at least one processor operatively coupled to user interface means, such as a display 102 and keyboard 104, and/or a cursor control, such as a mouse or a trackball 106, and storage media 108. The personal computer 100 may be a workstation that is accessible by more than one user. The personal computer 100 also includes a conventional processor 110, such as a Pentium® microprocessor manufactured by Intel, and conventional memory devices such as hard drive 108, floppy drive(s) 112, and memory 114.

Figure 1B:
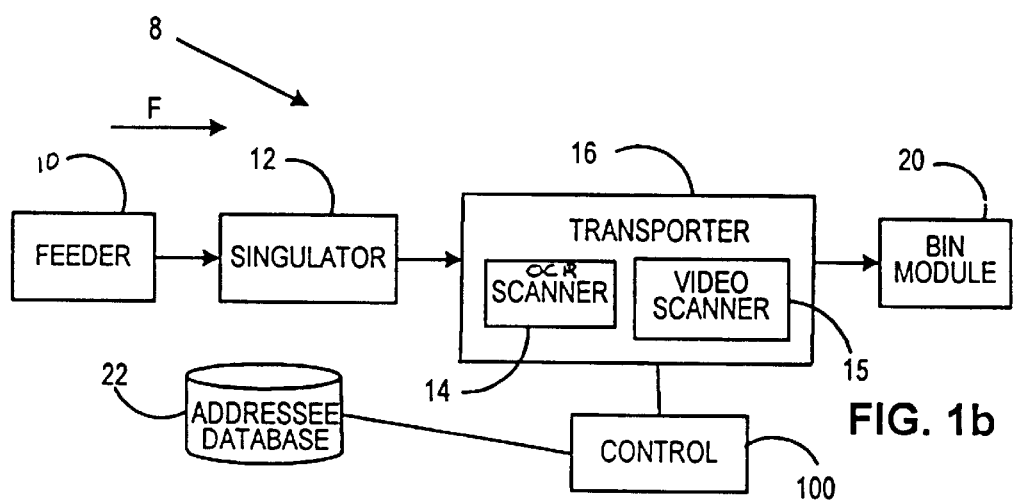
FIG. 1b illustrates the connection of the computer system to a mail sorting apparatus.
Figure 1C:
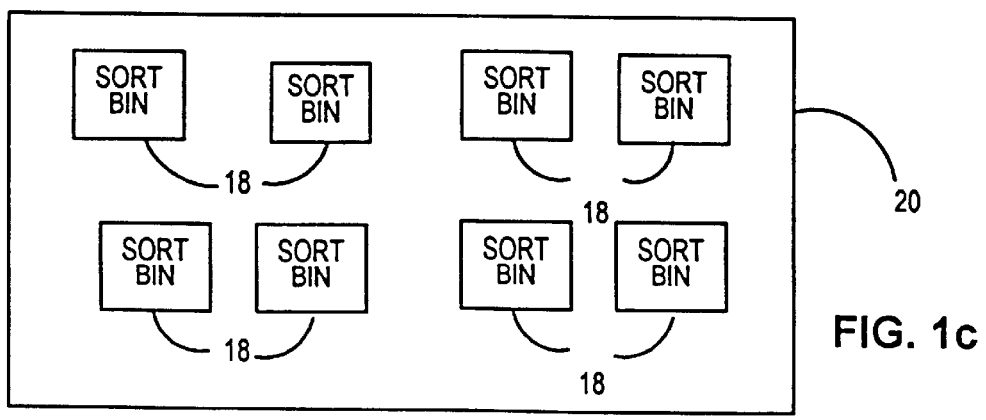
FIG. 1c is a block diagram illustrating a four bin module which may be part of the mailpiece sorting apparatus used to perform an embodiment of the present invention.

The computer system 100 can be connected to a sorting apparatus 8 as illustrated in FIG. 1b. The mailpiece sorting apparatus 8 may generally comprise a feeder 10, a line scan camera 14 (and optical character recognition (OCR) software, not shown), a mailpiece transporter 16, a bin module 20 (shown in FIG. 1c) with compartments or bins 18 for receiving sorted mailpieces 30 and a control system 100 which may be the microprocessor based personal computer system 100 described above. The computer system 100 includes appropriate memory devices 108, 114 for storage of information such as an address database 22. One of ordinary skill in the art would be familiar with the general components of the mail sorting apparatus 8.

The feeder 10 of mailpiece sorting apparatus 8 is designed to feed mailpieces of varying sizes, thicknesses and finishes and therefore, can singulate and feed variously configured incoming mailpieces including, for example, envelopes of various sizes, mailpieces up to ¾ inches thick, magazines, and variously configured small packages. The feeder's capability to handle such various mailpieces make it well suited for the present invention because of the need to singulate and sort mail which is of various sizes, thicknesses and finishes prior to additional processing. Such mailpieces are difficult to feed with a typical feeding apparatus.

Exemplary aspects of the feeder 10 of the system of the present invention are disclosed in the following: U.S. Pat. No. 5,971,391, issued Oct. 26, 1999 to Salomon et al. titled NUDGER FOR A MAIL HANDLING SYSTEM; U.S. Pat. No. 6,003,857, issued Dec. 21, 1999 to Salomon et al. titled SINGULATING APPARATUS FOR A MAIL HANDLING SYSTEM, U.S. Pat. No. 6,135,441 issued Oct. 24, 2000 to Belec et al. titled TWO STAGE DOCUMENT SINGULATING APPARATUS FOR A MAIL HANDLING SYSTEM; U.S. Pat. No. 6,217,020 issued Apr. 17, 2001 to Supron et al. titled METHOD AND APPARATUS FOR DETECTING PROPER MAILPIECE POSITION FOR FEEDING; and U.S. Pat. No. 6,328,300 issued Dec. 11, 2001 to Stefan et al. titled ALIGNER MECHANISM FOR A MAIL HANDLING SYSTEM and assigned to the assignee of the present invention and incorporated by reference herein.

The mailpiece sorting apparatus 8 and the OCR software may be used to determine the addressee of the mailpiece 30 or other information on the face of the mailpiece 30. The reading of various information may be performed with the assistance of intelligent character recognition (ICR) or imaging character recognition (OCRIIC) which may be part of the above mentioned OCR software and can read the various fields on the mailpiece 30.

Suspect/Harmful Mailpieces

Figure 2A:
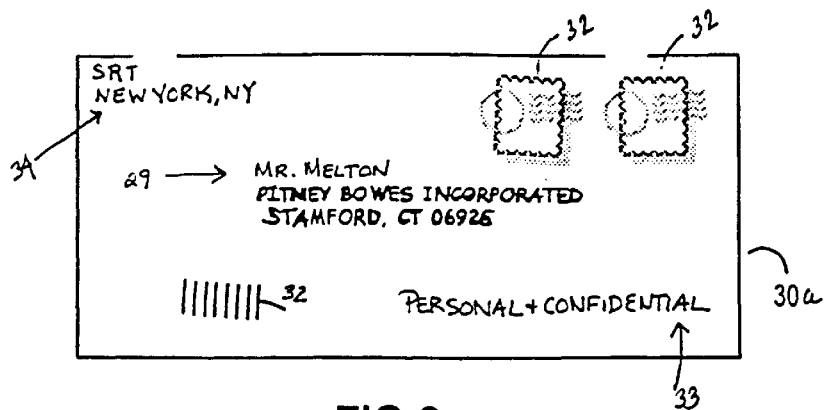
FIGS. 2a–b illustrate exemplary suspect mailpieces.
Figure 2B:
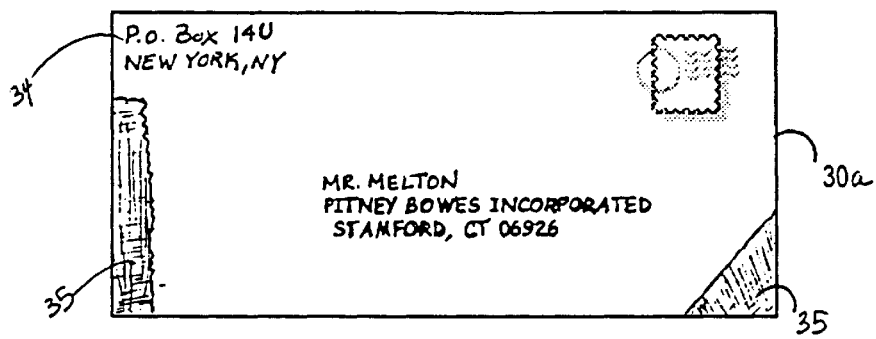

FIGS. 2a–d illustrate various examples of suspect mail 30a and trusted mail 30b. FIGS. 2a–b represent possibly suspect and/or harmful mailpieces. The Postmaster General of the United States has sent a message to postal customers across the country with criteria for suspect mailpieces. This United States Postal Service (USPS) criteria includes: 1) mail that is unexpected or from someone that you do not know; 2) mail that is addressed to someone no longer at your address; 3) mail that is handwritten and has no return address or bears a return address that cannot be confirmed; 4) mail that is lopsided or lumpy in appearance; 5) mail that is sealed with excessive amounts of tape; 6) mail that is marked with restrictive endorsements such as "personal" or "confidential"; and/or 7) mail that has excessive postage. The mailpiece of FIG. 2a is a possible suspect mailpiece because it has excessive postage 32 (i.e. multiple stamps), is addressed to an addressee 29 no longer at the address, bears the marking PERSONAL & CONFIDENTIAL 33 and has an unconfirmable return address 34 of SRT NEW YORK, N.Y. The mailpieces of FIG. 2b is a possible suspect mailpiece because it bears an unconfirmable return address 34 of PO BOX 14U, NEW YORK, N.Y.; is addressed to an addressee 29 no longer at the address, and is sealed with excessive amounts of tape 35.

In addition to the USPS criteria, Pitney Bowes, a company providing, leading-edge global, integrated mail and document management solutions for organizations of all sizes, and the assignee of the present invention, provides criteria at its web site www.pb.com. The criteria for suspect mail includes: 1) packages with excessive postage, using postage stamps as opposed to meter indicia; 2) addresses which are poorly typed or handwritten, and have misspellings; 3) packages which have oily stains, crystallization on wrapper or strange odors; 4) mail containing no return address or a return address not consistent with postmark; 5) mail which is exceptionally large or is a lopsided package; 6) a package which is rigid, bulky or discolored; 7) a package which displays evidence of electrical wire or tin foil; 8) a package which makes a sloshing sounds or appear to contain liquid; and 9) packages with excessive wrapping materials, such as masking tape, strapping tape, or string. Other organizations, such as law enforcement agencies or investigation authorities are also providing criteria for determining suspect mail including the Federal Bureau of Investigations (FBI).

Figure 2C:
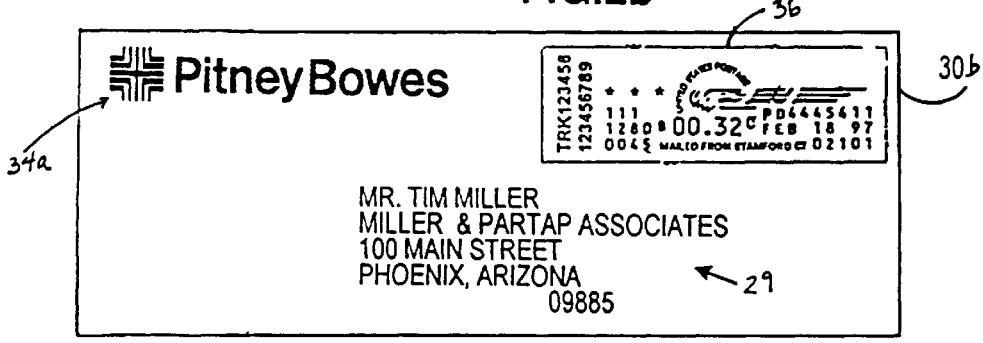
FIGS. 2c–d illustrate exemplary trusted mailpieces which include Pitney Bowes postage indicia that includes origin information.
Figure 2D:
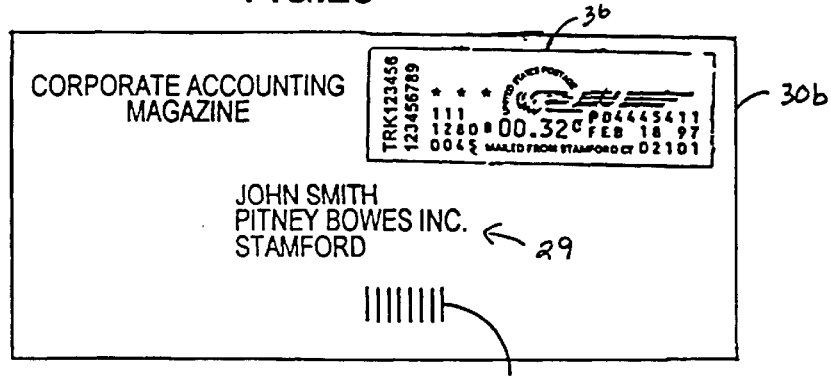

FIGS. 2c–d illustrate mail that is more trusted than those of FIGS. 2a–b. The mail 30b is trusted because postage (indicia 36) has been fixed to the mailpiece using a postage meter such as a Pitney Bowes electronic postage meter. Each Pitney Bowes postage meter imprint, includes, a tracking number that identifies the original point of mailing so recipient of mail can feel more comfortable receiving the mail since each piece has a unique fingerprint. Pitney Bowes Galaxy digital postage meters (not shown) can print indicia which includes various other information such as encrypted information in the indicia 36 of FIGS. 2c–d.

Figure 3:
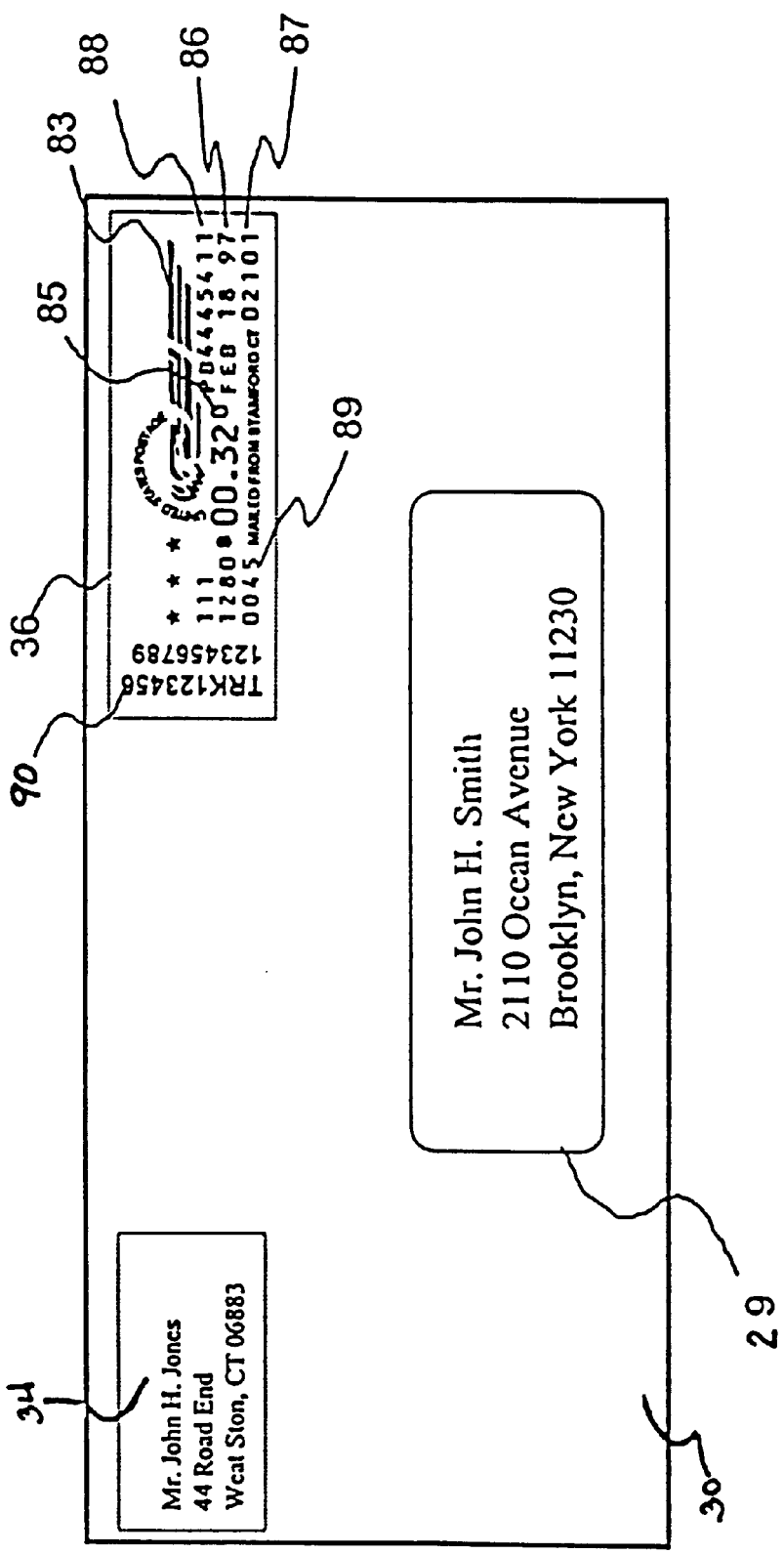
FIG. 3 is a drawing of a mailpiece containing a postal indicia that was affixed by an electronic meter.

FIG. 3 is a drawing of a mailpiece containing a postal indicia that was affixed by an electronic meter. Mailpiece 30 has a recipient address field 29 and a sender address field 8. A postal indicia 36 is affixed to mailpiece 30. Indicia 36 contains a dollar amount 85; the date 86 that postal indicia 36 was affixed to mailpiece 30; the place 87 that mailpiece 30 was mailed; the postal meter serial number 88; an eagle 83; a security code 89; and, a tracking number 7. Security code 89 and tracking number 90 are unique numbers that are derived from address field 29 and information contained in the postage meter that affixed indicia 36. The manner in which security code 89 and tracking number 90 are obtained is disclosed in the Sansone, et al. U.S. Pat. No. 4,831,555 titled UNSECURED POSTAGE APPLYING SYSTEM, assigned to the assignee of the present invention and herein incorporated by reference.

Figure 4:
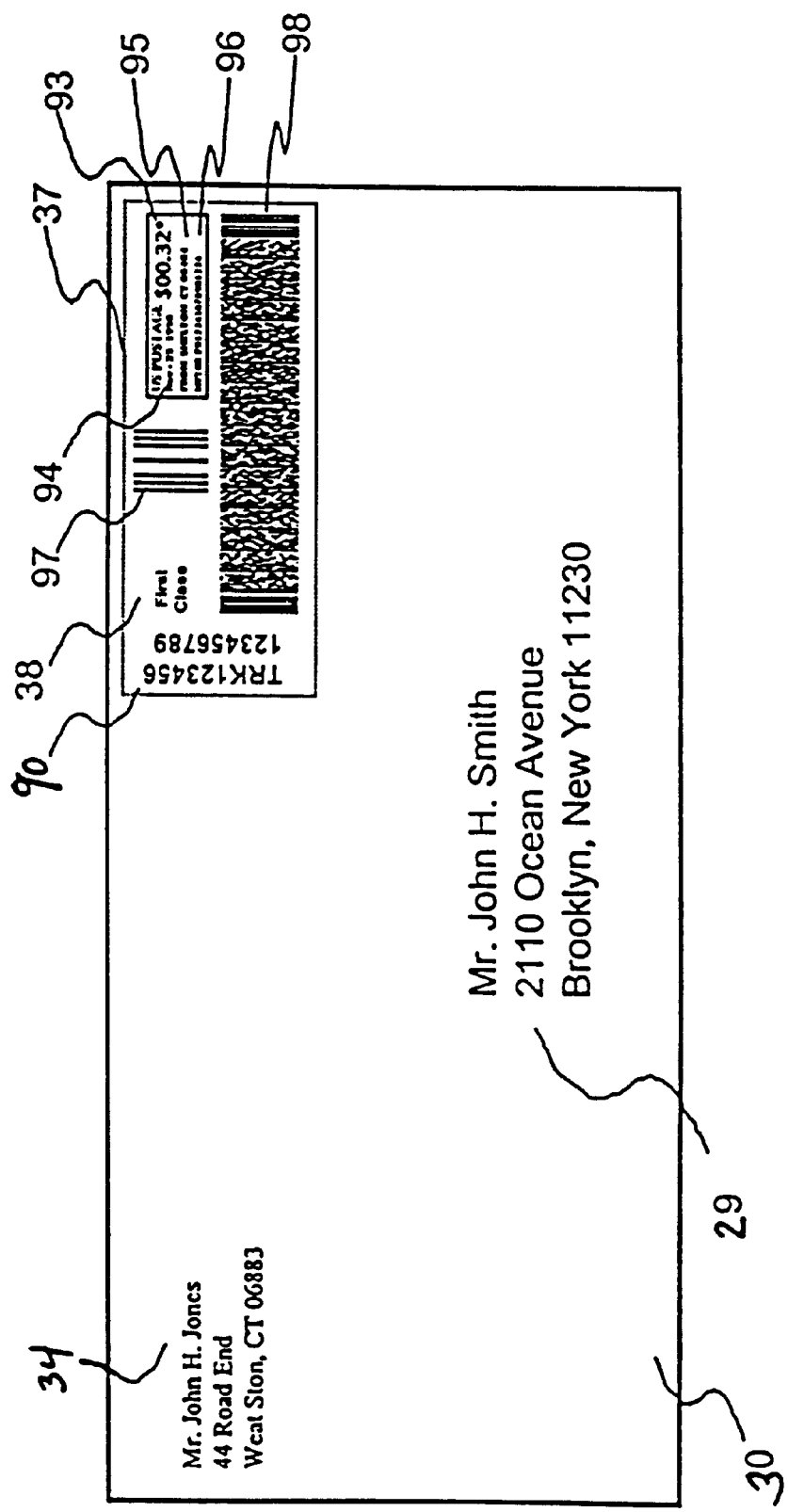
FIG. 4 is a drawing of a mailpiece containing an Information-Based Indicia.

FIG. 4 is a drawing of a mailpiece 30 containing a indicia 37. Mailpiece 30 has a recipient address field 29 and a sender address field 8. Mailpiece 30 contains USPS Information— Based Indicia (IBI) 37. The United States Postal Service Engineering Center has published a notice of proposed specification that describes a Information Based Indicia. The postal indicia 37 contains a dollar amount 93, the date 94, that the postal indicia was affixed to mailpiece 30, the place 95 that mailpiece 30 was mailed, the postal security device serial number 96, a FIM code 97; a 2D encrypted bar code 98; and a tracking number 7. Serial number 96 may be derived from bar code 98 or be equal to bar code 98. Bar code 98 is a unique number that is derived from address field 29 and information contained in the postal security device that affixed IBI 37. The manner in which information contained in bar code 98 is obtained is disclosed in the Sansone, et al. U.S. Pat. No. 4,831,555 titled UNSECURED POSTAGE APPLYING SYSTEM, assigned to the assignee of the present invention and herein incorporated by reference. Mailpiece 30 also contains an indication 38 of the class of mailpiece 30.

In addition to offering criteria for suspect mailpieces, Pitney Bowes offers guide lines for mail security practices so that companies can establish trust with their recipients. The guidelines include metering your mail such as with the Pitney Bowes indicia 36, using a clear identifiable return address such as a printed logo 34a, using postcards, avoiding sending samples, using tamper resistant seals, and using tape printed with your company name to seal packages.

System for Sanitizing and/or Sorting Mail

Figure 5A:
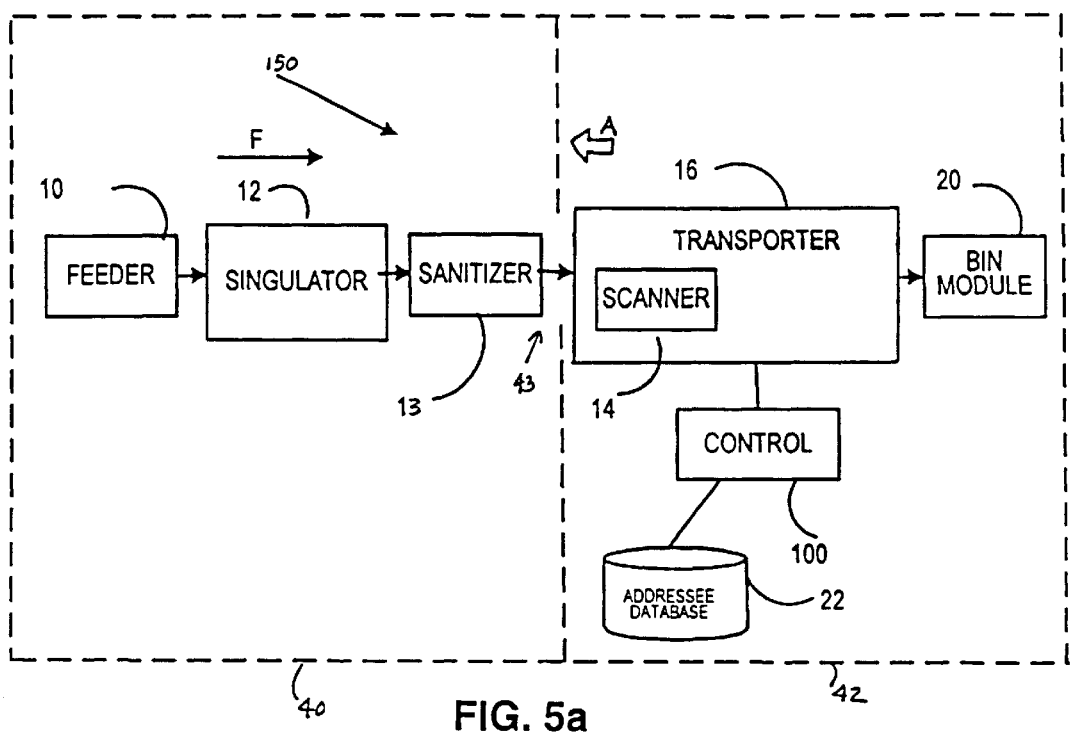
FIGS. 5a–e illustrates embodiments of the system of the present invention for sanitizing and sorting mail.
Figure 5B:
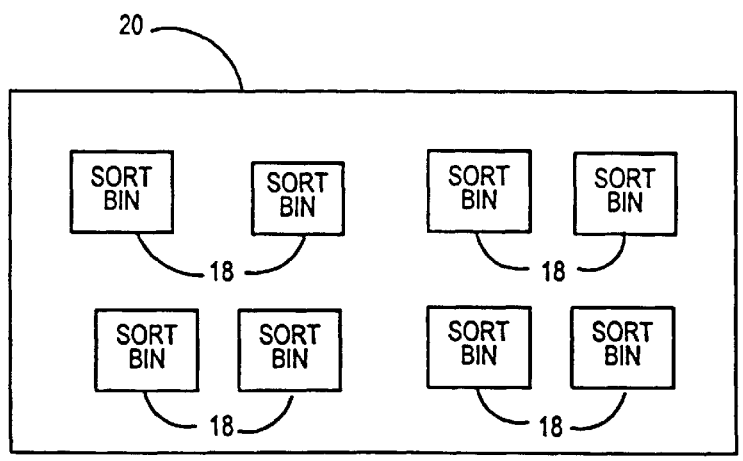

FIGS. 5a–e illustrates embodiments of the system the present invention for of sanitizing and sorting mail. FIG. 5a is an embodiment of a system 150 of the present invention for sanitizing and sorting mailpieces (referred to generally as mail or mailpieces 30 and includes mailpieces of various thicknesses and sizes such as mailpieces in an incoming mail stream). The system 150 of the present invention includes a feeder 10 for feeding mailpieces 30 (not shown) from a stack, a singulator 12 for separating mailpieces, a sanitizer 13 for sanitizing mailpieces (sanitization can include for example killing biohazardous material in mailpieces 30 by means of microwave technology, irradiation, ultraviolet light, ozone, chemical mist or other technology that will kill the biohazardious material in the mailpiece without harming the letter/material content of the mailpiece). Many sanitization technologies can only sanitize objects of relatively slim thicknesses, therefore, by the present invention mailpieces are singulated prior to passing through sanitization area 44. The system 150 further includes a transporter 16, a scanner 14 (such as a scanner for an optical character recognition (OCR) system), a control system 100 (such as the control system of FIG. 1*a*), an addressee database 22 and a bin module 20 which is shown in further detail in FIG. 5*b* to include individual sort bins 18. While eight sort bins 18 are shown in FIG. 5*b* it should be understood that the number of sort bins 18 can be varied according to the needs of a sort plan used for determining the destination bin for each of the mailpieces 30 in the stack.

In an alternate embodiment, shown with dashed lines, a sanitization room 40 can contain the feeder 10, singulator 12 and sanitizer 13 and a clean room 42 can include transporter 16, scanner 14, control 100 with database 22 and bin module 20. Other configurations for separating sections of the system 150 into sanitization area 40 and clean area 42 could be performed. The purpose of separating components of the system is to minimize exposure to and contain possible harmful elements that are emitted from or are in the mail stream. Operators stationed in the sanitization area 40 can be outfitted with personal protective equipment such as respirators, lab coats and protective clothing, eye and face protection and gloves. The clean room 42 is configured so that air flow between the clean room 42 and the sanitization area 40 is from the clean room 42 to the sanitization area 40 (thus the sanitation area has a negative pressure as compared to the clean room). The direction of air flow from clean room 42 to sanitization area 40 is shown by arrow A. Appropriate filtration and sealing can be provided in transition area 43 of the feed path F that is a passage between the clean room 42 and sanitization area 42. A containment module (not shown), for example, can be placed around that area with filtration devices and an opening along the feed path F to accommodate the largest mailpiece which can be sorted by the system. Operators of the sanitization room can be trained in appropriate safety practices including entrance and exit protocol, biohazard containment and proper attire.

Figure 5C:
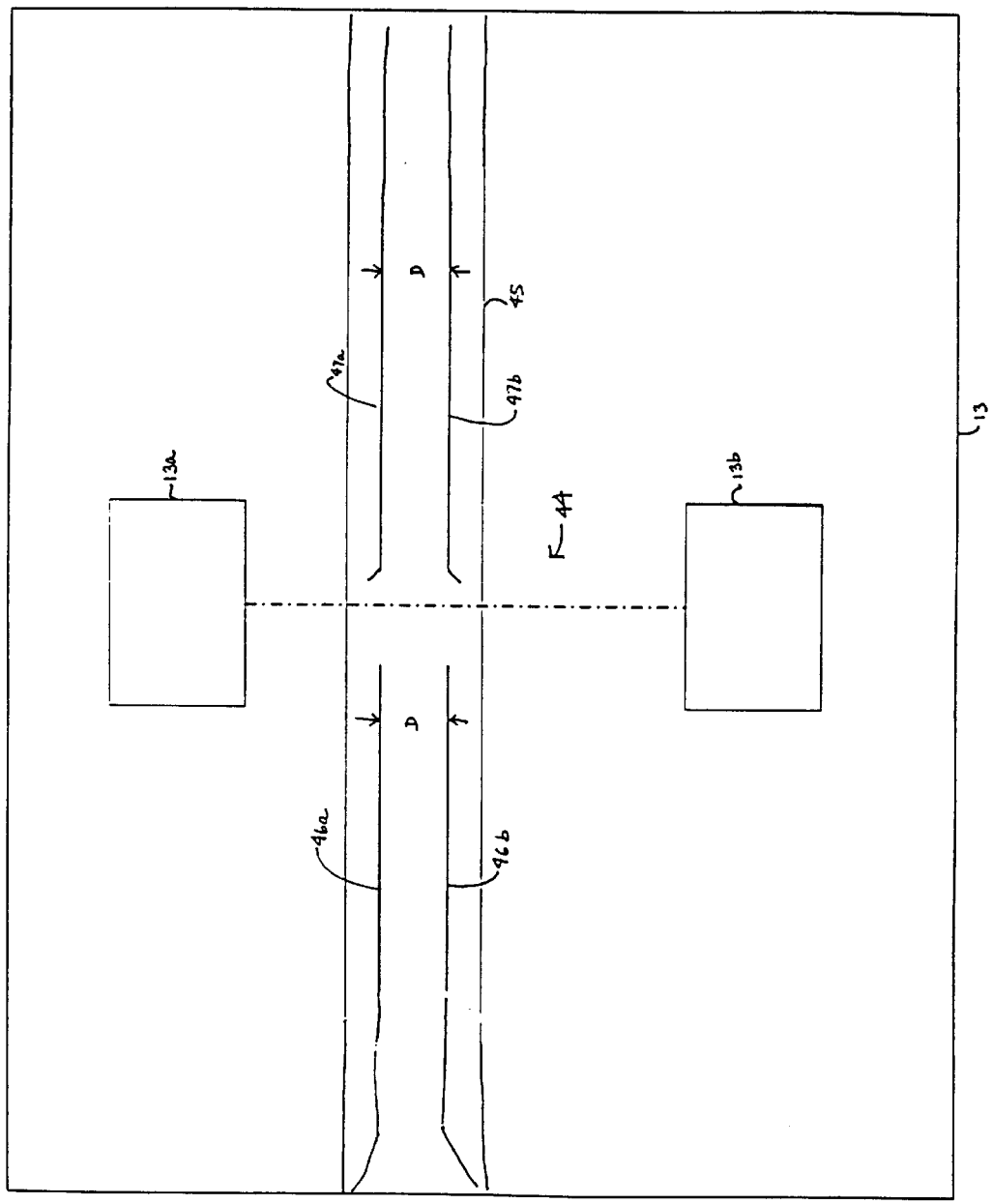

Sanitizer 13, in addition to including sanitizing apparatus (shown generally as 13*a* and 13*b* with a sanitization area 44 denoted generally as a dashed line between modules 13*a* and 13*b*) described below can be configured in such a way as to transport singulated mailpieces past a sanitization area 44. This can be done for example using a configuration as shown in FIG. 5*c* which includes a transport belt 45 for moving mailpieces and conveyor. In the sanitizer 13, the mailpieces 30 are driven along their bottom edges by a transport belt 45 along feed path F. The gap D between the guide walls 46*a* and 46*b* and 47*a* and 47*b* allows that the frictional forces between the mailpieces are almost nonexistent. Since the frictional forces tend to cause multi-mailpiece feeds, this configuration helps to prevent multi-mailpiece feeds from occurring. Furthermore, the sanitizing station acts as a buffer allowing mailpieces to deskew or register onto the transport belt 45. Subsequent to passage through the sanitizing station 13 the individual mailpieces are transported into the next segment of the system 150, the transport station 16.

In the preferred embodiment, the distance D between guide walls 46*a–b* and 47*a–b* is approximately 28 millimeters. This allows for the passage of ¾" thick mailpieces. However, other mailpiece thickness specifications and distances may be used. The minimum distance may be determined by the specification of the maximum width of mailpieces to be passed along the document feed path F. Additionally, the distance is determined by the minimum angle that the smallest mailpiece would have with respect to the transport belt 45 when leaning against guide walls 46*a–b* or 47*a–b*. The angle, if too small, would cause the mailpiece to lean below the sanitization area.

In an alternate embodiment (illustrated in FIG. 5*d*), instead of guide walls, vertically oriented transport belts 48*a–b* and vertically oriented transport belts 49*a–b* are positioned parallel to and on each side of the transport belt 45 along feed path F. The vertically oriented belts are driven in the direction of the feed path F and serve to move the mailpieces along the feed path F as well as provide support for the mailpieces in a similar fashion to the guide walls 46*a–b* and 47*a–b*. An expanded view of a typical configuration for vertically oriented transport belts 49*a–b* is shown in FIG. 5*e*. A similar configuration may be used for vertically oriented transport belts 48*a–b*.

The sanitizer 13 for sanitizing mailpieces can include, for example, technology for killing biohazardous material such as Anthrax, contained in mailpieces 30 by means of microwave technology, irradiation, ultraviolet light, ozone, chemical mist or other technology that will kill the biohazardous material in the mailpiece without harming the letter/material content of the mailpiece).

Figure 6:
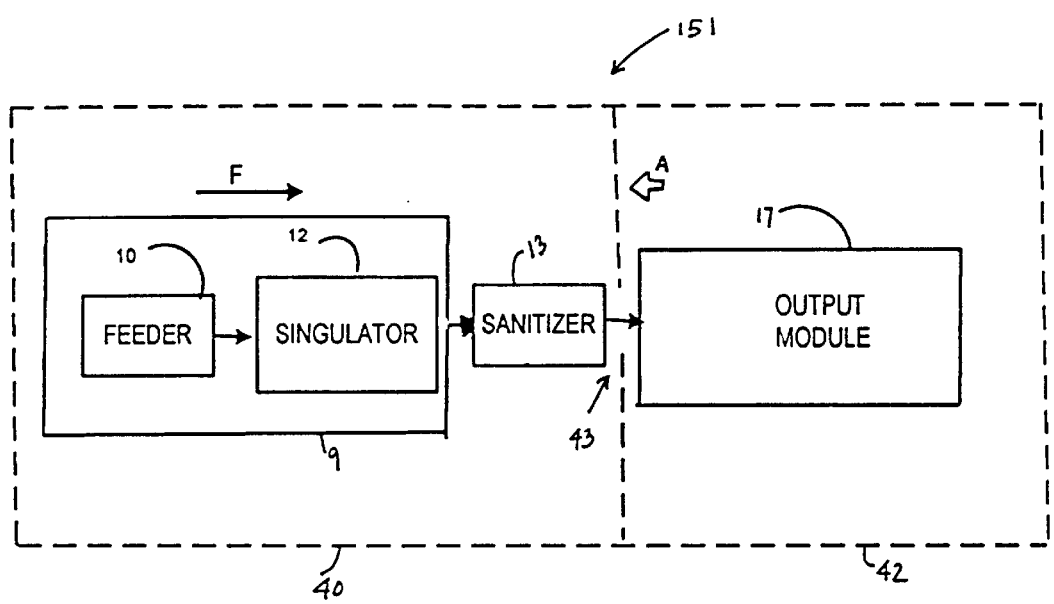
FIG. 6 illustrates an embodiment of the system of the present invention for sanitizing mail.

FIG. 6 illustrates an embodiment of the system 151 of the present invention for sanitizing mail. The system 151 is a less costly system than that of system 150 since the system 151 does not include sortation components such as a sort plan, OCR system 14 and bin modules 20. The system 151 comprises a separation module 9 which includes feeder 10 and singulator 12. Down stream of separation module 9, along feed path F is sanitizer 13 followed by output module 17 for collecting the sanitized mailpieces 30. The sanitizer 13 for sanitizing mailpieces can include, for example, technology for killing biohazardous material such as Anthrax, contained in mailpieces 30 by means of microwave technology, irradiation, ultraviolet light, ozone, chemical mist or other technology that will kill the biohazardous material in the mailpiece without harming the letter/material content of the mailpiece). The output module 17 could be for example, a cart, a bucket, a stacker such as a horizontal or vertical stacker or other suitable component. Alternately, the diverter and stacker modules can be integrated.

In the present embodiment of the system of the present invention where mailpieces are moved along the feed path F in a vertical or on edge orientation, the output or collection module 17 could be an on-edge mail stacking system comprising a transport followed by various stacking mechanisms. Generally, a multi-bin on-edge stacking system includes gating mechanisms which divert specific mailpieces into predetermined stacker bins (not shown). Typically, mailpieces are transported vertically along a dual belt transport system, deflected into a stacker bin by a deflector mechanism, and guided into the bin by conventional guide and urging components. The objective of mail stacking systems is to produce one or more bundles of mailpieces.

In an alternate embodiment, shown with dashed lines, the sanitization room 40 can contain the separation module 9 (including feeder 10 and singulator 12) and sanitizer 13 and the clean room 42 can include output module 17. Other configurations for separating sections of the system 150 into sanitization area 40 and clean area 42 could be performed. The purpose of separating components of the system is to minimize exposure to and contain possible harmful elements that are emitted from or are in the mail stream. Clean room technology is explained generally above, note that in FIG. 6 the direction of air flow is from clean room 42 to sanitization area 40 and is shown by arrow A.

System for Detecting the Presence of Harmful Materials in Mail

Figure 7A:
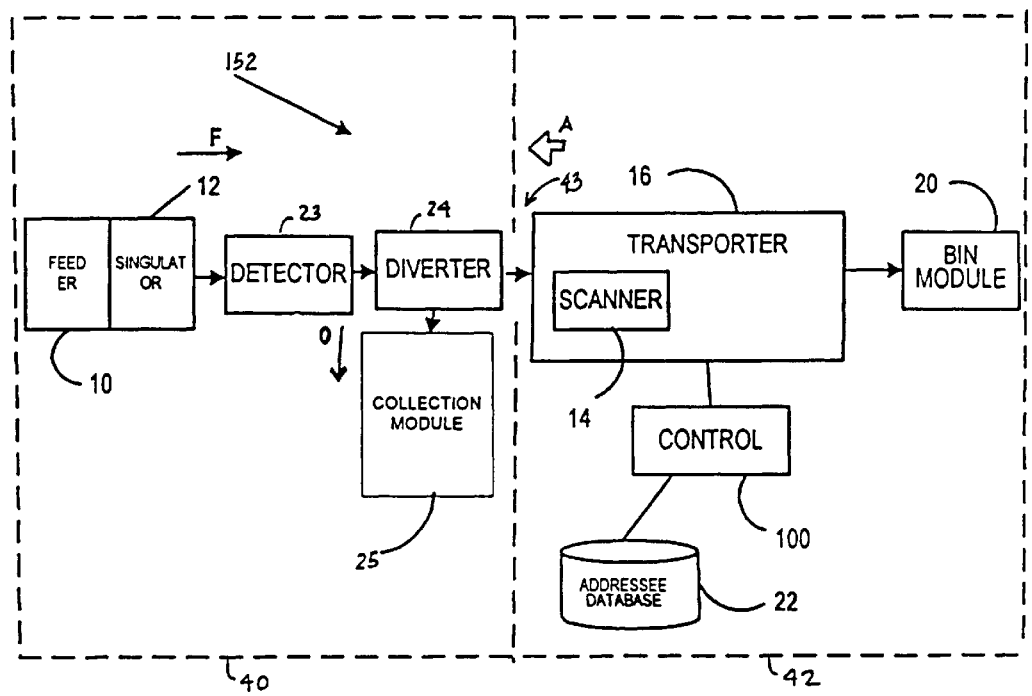
FIGS. 7a–b illustrate an embodiment of the system of the present invention for detecting life harming substances in mail and diverting such mail from the mail stream.
Figure 7B:
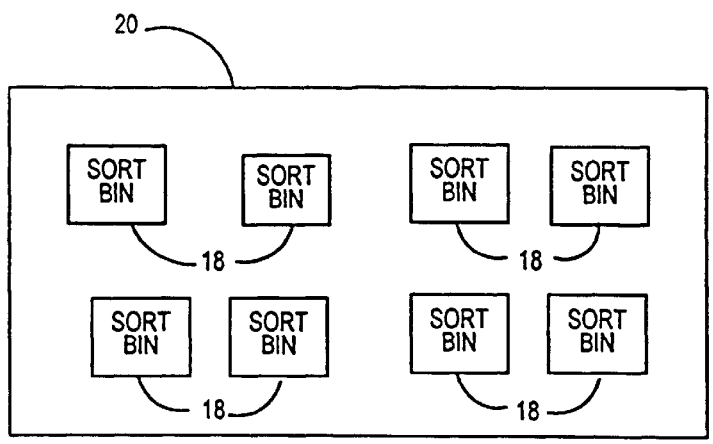

FIGS. 7a–b illustrates embodiments of the system 152 of the present invention for detecting life harming substances in mail and diverting such mail from the mail stream. The system 152 comprises a feeder 10, singulator 12, detector 23 for detecting the presence of harmful materials, diverter 24 for diverting mailpieces for which the presence of life harming materials has been detected (hereinafter harmful mailpieces). The diverter 24 diverts the harmful mailpieces to collection module 25 and is typically configured such that a finger or van (not shown) diverts mailpieces from the feed path F to an out sorting path O. Mailpieces for which no presence of life harming materials has been detected (hereinafter clean mailpieces) remain along feed path F and continue through transporter 16 to appropriate sort bin 18 (shown in FIG. 7b) of bin module 20. In an alternate embodiment of the present invention, multiple diverters and stackers can be used such that each diverter is designated for diverting a particular category of mailpiece. As described above the control system 100, addressee database 22 (the addressee database has various fields that contain addressee information including for example an addressee name field and an associated addressee location field) and a sort plan are used to make a determination of the appropriate sort bin 18 (associated with the addressee location field) for delivery of the mailpiece.

Alternately, the diverter and stacker modules can be integrated. In the present embodiment of the system of the present invention where mailpieces are moved along the feed path in a vertical or on edge orientation, the output or collection module 17 could be an on-edge mail stacking system comprising a transport followed by various stacking mechanisms. Generally, a multi-bin on-edge stacking system includes gating mechanisms which divert specific mailpieces into predetermined stacker bins (not shown). Typically, mailpieces are transported vertically along a dual belt transport system, deflected into a stacker bin by a deflector mechanism, and guided into the bin by conventional guide and urging components. The objective of mail stacking systems is to produce one or more bundles of mailpieces.

In an alternate embodiment, shown with dashed lines, the detection room 41 can contain the feeder 10, singulator 12 and sanitizer 13 and the clean room 42 can include transporter 16, scanner 14, control 100 with addressee database 22 and bin module 20. Other configurations for separating sections of the system 152 into detection room 41 and clean room 42 could be performed. The purpose of separating components of the system is to minimize exposure to and contain possible harmful elements that are emitted from or are in the mail stream. Operators stationed in the sanitization area 40 can be outfitted with personal protective equipment such as respirators, lab coats and protective clothing, eye and face protection and gloves. The clean room 42 is configured so that air flow between the clean room 42 and the detection room 41 is from the clean room 42 to the detection room 41 (thus the detection room 41 has a negative pressure as compared to the clean room 42). The direction of air flow from clean room 42 to detection room 41 is shown by arrow A. Appropriate filtration and sealing can be provided in transition area 43 of the feed path F that is a passage between the clean room 42 and detection room 41. A containment module (not shown), for example, can be placed around that area with filtration devices and an opening along the feed path F to accommodate the largest mailpiece which can be sorted by the system. Operators of the detection room 41 can be trained in appropriate safety practices including entrance and exit protocol, biohazard containment and proper attire.

Figure 5D:
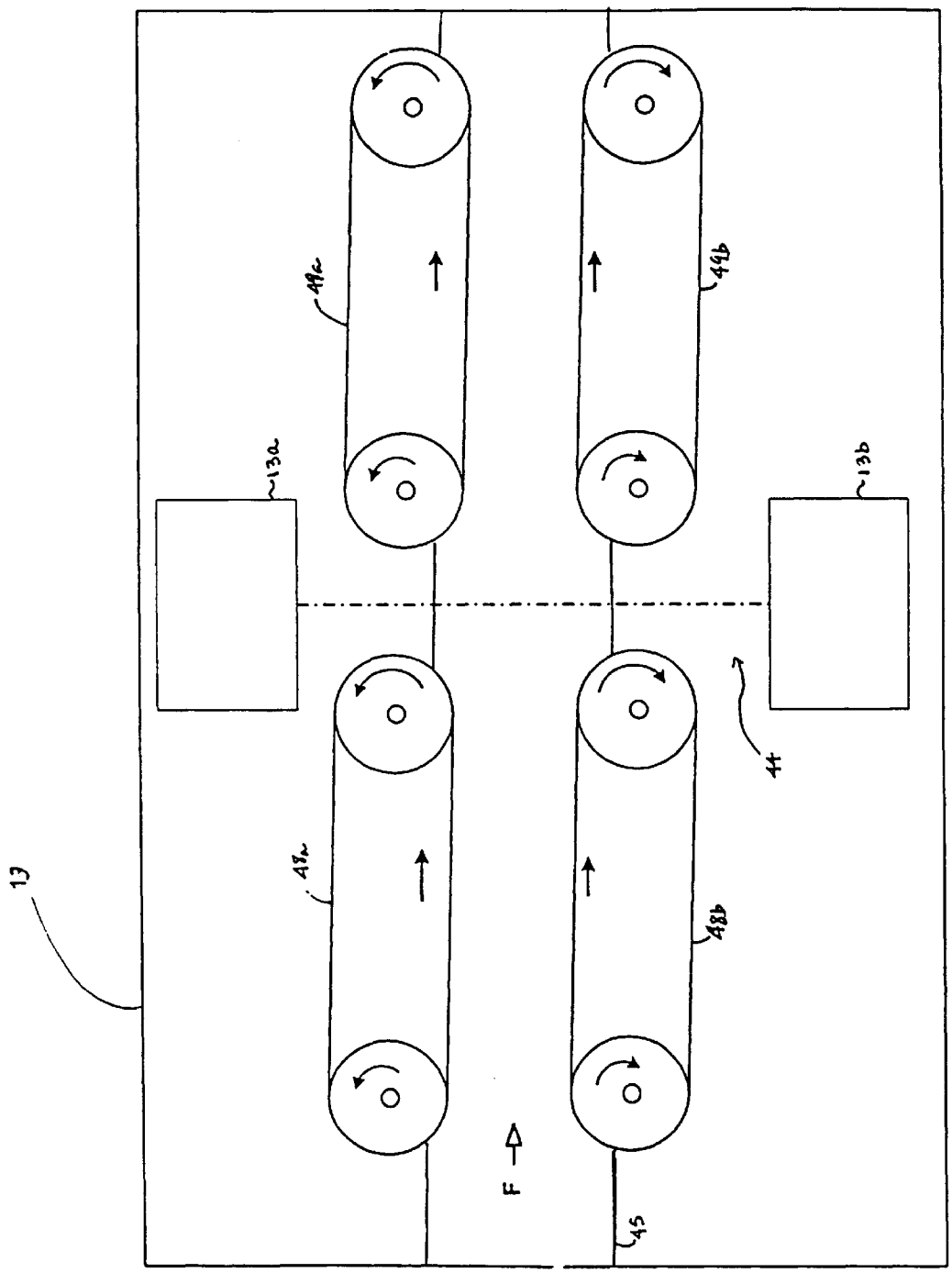
Figure 5E:
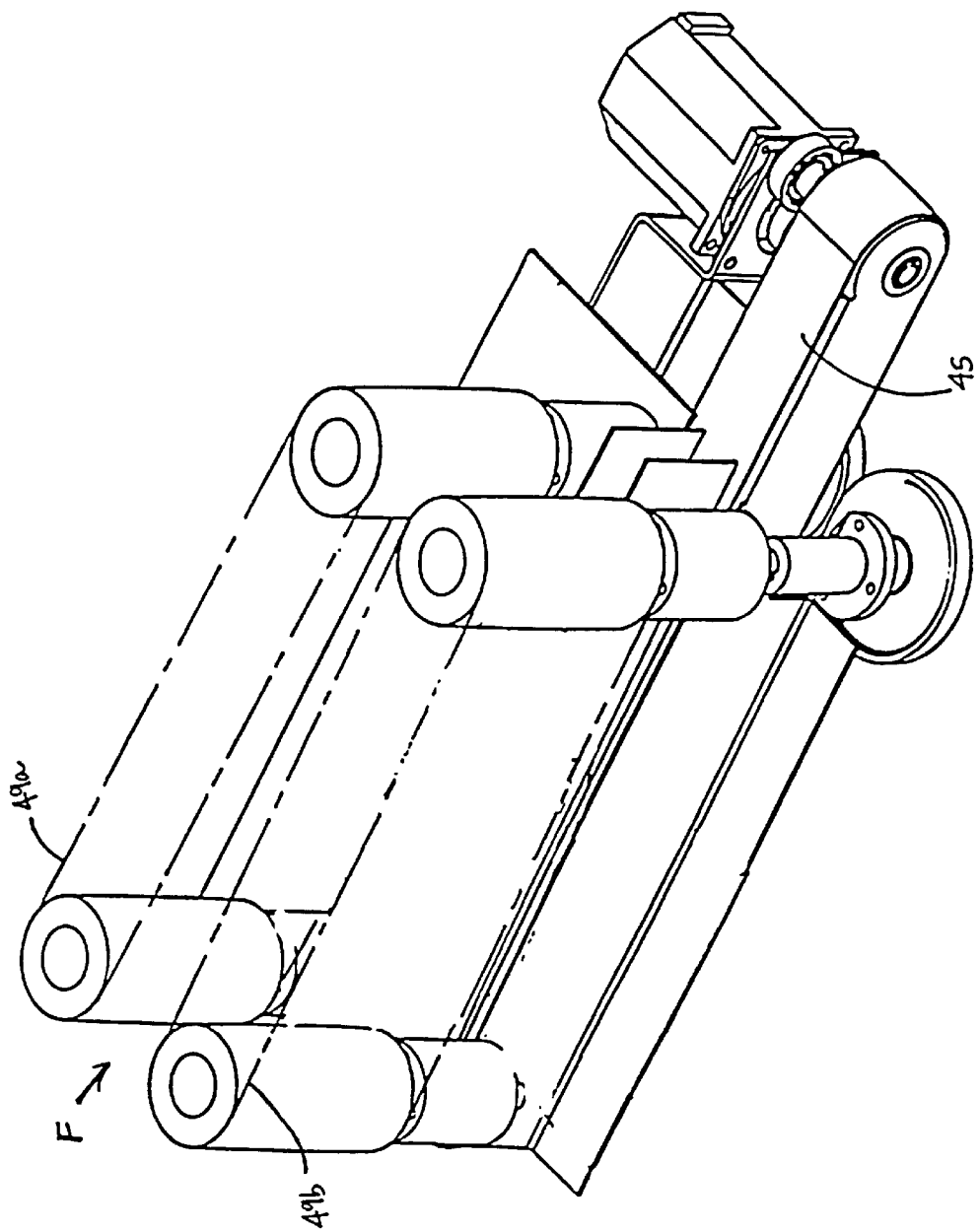

The detector 23 can be configured similarly to the sanitizers of FIGS. 5c and 5d so as to move mailpieces along feed path F the gap between walls or vertically oriented belts. Detection occurs in area 44 between components 13a and 13b which in this embodiment are detection apparatus. The detector be configured to detect for example biohazardous materials or explosives. The output module 25 could be for example, a cart, a bucket, a biohazardous materials container, a stacker such as a horizontal or vertical stacker (the general components of a stacker for handling mixed sized mailpieces are described U.S. Pat. No. 6,161,830 titled METHOD AND APPARATUS FOR STACKING MIXED MAIL issued to Yap on Dec. 19, 2000, assigned to the assignee of the present invention and herein incorporated by reference) or other suitable component such as a bin for containing biohazardous materials or an explosives container.

Figure 8A:
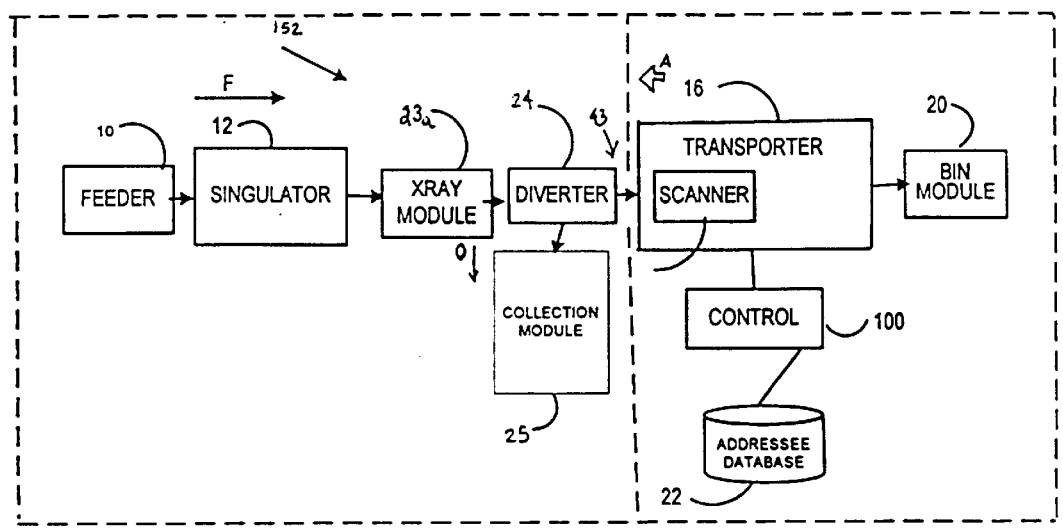
FIGS. 8a–b illustrates embodiments of the system of the present invention for detecting life harming substances in mail, through the use of x-ray, and diverting such mail from the mail stream.
Figure 8B:
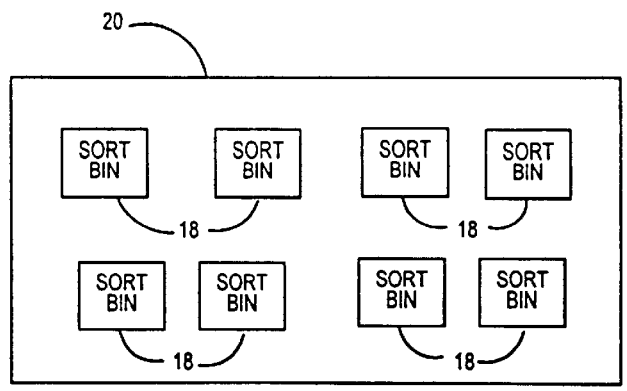

In an alternate embodiment shown in FIGS. 8a–b, the detector can be an x-ray module 23a. X-ray technology can be used to screen mailpieces for suspicious content. X-rays generally indicate the density of materials contained in the article being x-rayed. An x-ray of a mailpiece can be used, for example, to detect materials such as powders, plastics, electronics and wires or other potentially life threatening materials. A method can be used to interpret an x-ray of the mailpieces by interpreting the x-ray image. If the x-ray image contains portions that are interpreted to be suspect, then the system can divert the mailpiece to collection module 25. The system 152 of FIG. 8a can also include the detection room 41 and clean room 42 configuration described above, with air flow between the detection room and the clean room shown generally with arrow A.

The present invention provides detection of harmful materials and diversion of mailpieces suspected of containing harmful materials from the mailstream. It does not address the issue of cross contamination of the mailpieces. It is assumed that since detection is performed after mailpieces have been singulated that if mailpieces have been cross contaminated, the contamination will be detected for each individual mailpiece as it passes through detection module 23.

System and Method for Outsorting Suspect Mail From a Mail Stream

Figure 9A:
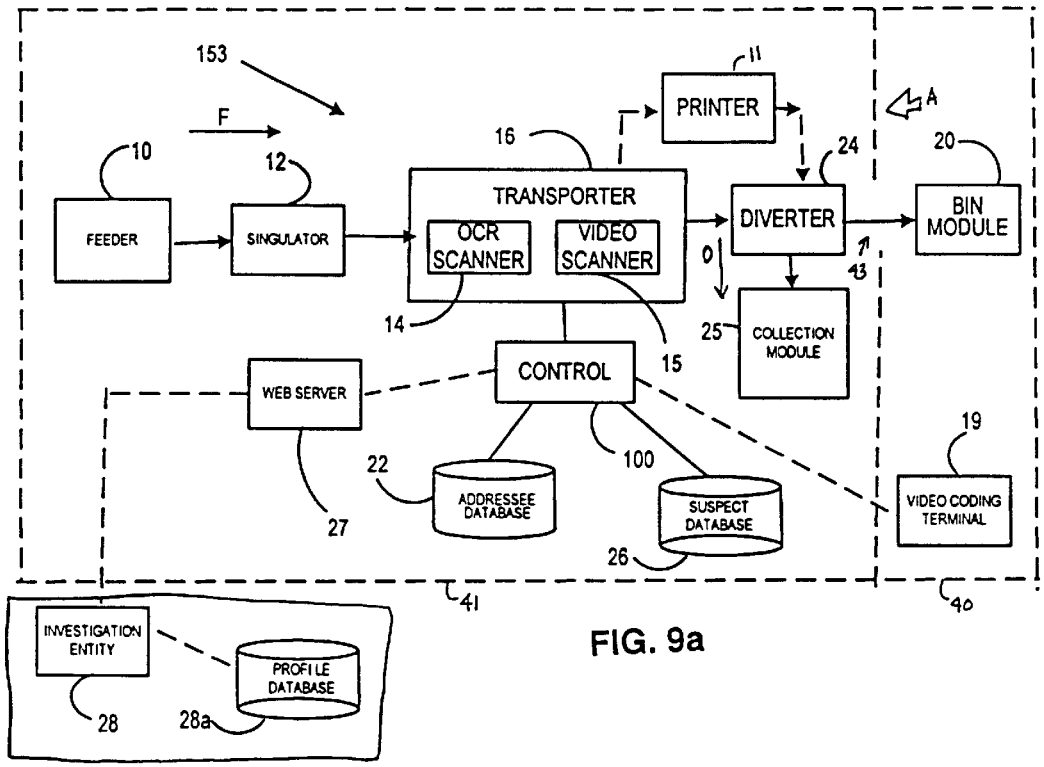
FIGS. 9a–b illustrate an embodiment of the system of the present invention for detecting or predicting suspect mailpieces in a mail stream and diverting such mailpieces from delivery.
Figure 9B:
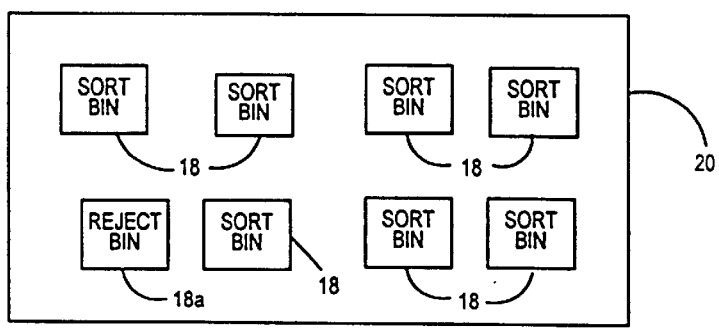

FIGS. 9a–b illustrate an embodiment of the system of the present invention for detecting or predicting suspect mailpieces in a mail stream and diverting such mailpieces from delivery. FIG. 9c illustrates an embodiment of the method the present invention for detecting or predicting suspect mailpieces in a mail stream and diverting such mailpieces from delivery.

FIG. 9a illustrates a system 153 for detecting (or predicting) and out sorting suspect mail from a mail stream. The system 153 includes a feeder 10, singulator 12, transporter 16, optical character recognition (OCR) scanner 14, video scanner 15, control system 100, addressee database 22 for use with a sort plan and a suspect database 26 that includes criteria for determining whether a mailpiece is suspected of containing life harming substances. The suspect database is used in the method illustrated in FIG. 9c for detecting suspect mailpieces in a mail stream and diverting such mailpieces from delivery. Downstream from the transporter 16 along the feed path F, the diverter module 24 is positioned to divert mailpieces into collection module 25. The diverter 24 diverts the suspect mailpieces to collection module 25 and is typically configured such that a finger or van (not shown) diverts mailpieces from the feed path F to an out sorting path O. Collection module 25 could be for example, a cart, a bucket, a biohazardous materials container, a stacker such as a horizontal or vertical stacker (the general components of a stacker for handling mixed sized mailpieces are described U.S. Pat. No. 6,161,830 titled METHOD AND APPARATUS FOR STACKING MIXED MAIL issued to Yap on Dec. 19, 2000, assigned to the assignee of the present invention and herein incorporated by reference) or other suitable component such as a bin for containing biohazardous materials or an explosives container. Bin module 20 is positioned downstream from diverter 24 for collecting trusted mailpieces in appropriate bins 18 (shown in FIG. 9b) as determined by the sort plan.

In an alternate embodiment of the present invention, multiple diverters and stackers can be used such that each diverter is designated for diverting a particular category of mailpiece.

Alternately, the diverter and stacker modules can be integrated. In the present embodiment of the system of the present invention where mailpieces are moved along the feed path F in a vertical or on edge orientation, the output or collection module 17 could be an on-edge mail stacking system comprising a transport followed by various stacking mechanisms. Generally, a multi-bin on-edge stacking system includes gating mechanisms which divert specific mailpieces into predetermined stacker bins (not shown). Typically, mailpieces are transported vertically along a dual belt transport system, deflected into a stacker bin by a deflector mechanism, and guided into the bin by conventional guide and urging components. The objective of mail stacking systems is to produce one or more bundles of mailpieces.

In an alternate embodiment, shown with dashed lines, the detection room 41 can contain the feeder 10, singulator 12, transporter 16, OCR scanner 14, video scanner 15, control 100 with addressee database 22 and suspect database 26, and diverter module 25 connected to collection module 25. The clean room 42 can include bin module 20. Other configurations for separating sections of the system 153 into detection room 41 and clean room 42 could be performed. The purpose of separating components of the system 153 is to minimize exposure to and contain possible harmful elements that are emitted from or are in the mail stream. Air flow between the detection room 41 and the clean room 40 is shown generally with arrow A. The purpose of separating components of the system 153 is to limit exposure to and contain possible harmful elements that are emitted from or are in the mail stream. Operators stationed in the sanitization area 40 can be outfitted with personal protective equipment such as respirators, lab coats and protective clothing, eye and face protection and gloves. The clean room 42 is configured so that air flow between the clean room 42 and the detection room 41 is from the clean room 42 to the detection room 41 (thus the detection room 41 has a negative pressure as compared to the clean room 42). Appropriate filtration and sealing can be provided in transition area 43 of the feed path F that is a passage between the clean room 42 and detection room 41. A containment module (not shown), for example, can be placed around that area with filtration devices and an opening along the feed path F to accommodate the largest mailpiece which can be sorted by the system. Operators of the sanitization room can be trained in appropriate safety practices including entrance and exit protocol, biohazard containment and proper attire.

FIG. 9c illustrates an embodiment of the method of the present invention for detecting or predicting suspect mailpieces in a mail stream and diverting such mailpieces from delivery. At step S200 the method begins. At step S202 a stack of mailpieces (not shown) is placed on the feeder 10 of the system 153 and the feeder 10 is set to auto feed. At step S204 the mailpieces 30 are moved along the feed path F and a leading mailpiece is obtained from the singulating device. At step S206 the mailpiece 30 is read using OCR scanner 14 and/or video scanner 15. At step S208 information read from the mailpiece is compared to information in suspect database 26. The suspect database contains various criteria such as the criteria described above (under the heading SUSPECT/HARMFUL MAILPIECES) for determining a suspect mailpiece. The system 153 also comprises software for performing the decision making process as to whether the mailpiece is suspect, such as is asked in the query of step S210. The software can be written such that when it is determined that a mailpiece meets a particular percentage of the criteria stored in suspect database 26 then the mailpiece is concluded to be suspect.

Tape on the mailpiece could be detected with an optical scanner which comprises a light source, a lens and sensor (not shown) integrated into the document scanner module. The optical scanner can be a Pl200MC-C module manufactured by Peripheral Imaging Corporation of San Jose, Calif. The optical scanner has high accuracy of about 200 to 300 dpi. The optical scanner is able to scan a variety of mailpieces and is connected to a system controller 100 which processes information outputted by the scanner. The optical scanner could sense the tape area, such as a shiny or matte area of the envelope, by detecting the optical difference between the tape area and the non-tape area. The tape modifies the surface characteristics of the mailpiece, resulting in a difference in optical response as detected by the sensor.

If it is determined at the query of step S210 that the mailpiece is not suspect, then at step S210a the system 153 uses addressee database 22 and a sort plan to determine the appropriate bin 18 for delivery of mailpiece. This determination is not the subject of the present invention and is made generally as follows: 1) the system 153 makes a comparison of information obtained by the OCR system with the addressee database 22 to attempt to find an addressee match; 2) a query is made as to whether an addressee match has been made; 3) if an addressee match has been made, the mailpiece is delivered to appropriate bin 18; and 4) if an addressee match has not been made, mailpiece are delivered to, for example a reject bin 18a. Reject mailpieces may be processed further using other methods such as, for example, video coding or voice recognition. At step S210b the mailpiece, which could be for example trusted mailpiece trusted mailpiece 30b as illustrated in FIGS. 2c–d, is delivered to the appropriate sort bin 18.

Returning to the query of step S210, if the answer to the query is yes then the mailpiece is suspect and at step S212 the mailpiece is diverted to collection module 25 (described above) by diverter 24. In an alternate embodiment, shown with dashed lines, when the mailpiece is determined to be suspect at step S210, then at step S211 an identification (ID) code 32 (shown in FIG. 2a) is printed on the mailpiece and may be read in subsequent sorting passes. The printing is performed using a printer module 11 situated along the feed path F of the system 153 upstream from diverter 24. The printer module 11 is shown with dashed lines in FIG. 9a. In the alternate embodiment, after step S211, the suspect mailpiece 30a is diverted to collection module 25 (described above) by diverter 24.

Steps S211, S212 and S210b are each followed by step S214 where a query is made as to whether there are more mailpieces to be processed. If the answer to the query of step S214 is yes, then steps S204 through S212 are repeated as appropriate until there are no more mailpieces to be processed. If the answer to the query of step S214 is no, then at step S218 the method ends.

In an alternate embodiment, shown with dashed lines, after the query of step S214 if there are no more mailpieces to be processed then at step S215a suspect mailpieces are retrieved from the diverter collection bin and delivered to a sanitization/processing area (not shown) (or the diverter collection bin containing the suspect mailpieces is transported to a sanitization/processing area). The sanitization/processing area is configured to process mailpieces such, for example to biohazardous material in the mailpiece and is described above in the description of system 153. Next at step S215b the suspect mailpieces are sanitized/processed. Following sanitization/processing, the mailpieces determined to be safe can be resorted for delivery to the appropriate bin 18, such determination is made using addressee database 22 and the sort plan. Next at step S218 the method ends.

In another alternate embodiment, shown with dashed lines, at step S217a an image of the suspect mailpiece is sent to a video coding terminal 19 (shown with dashed lines in FIG. 9a). Next at step S217b, an operator of the video coding terminal 19 makes a final determination as to the suspect status of the mailpiece. The query is made to the operator at step S217c as to whether the mailpiece is suspect. If the operator determines the mailpiece to be suspect, such information is tagged to the mailpiece ID code 32 (which was printed in alternate step S211 onto the suspect mailpiece 30a). If the operators determines that the mailpiece is not suspect, then at step S217e the operator tags the mailpiece ID code 32 (printed in alternate step S211) to indicate non-suspect mailpiece/delivery to appropriate bin. At step S217f following steps S217d and steps S217e, a query is made as to whether there are more images to be processed. If the answer to the query of step S217f is yes, then steps S217a–e are repeated as appropriate. If the answer the query of S217f is no, then at step S217g the suspect mailpieces are resorted for delivery as indicated by information tagged to the mailpiece ID code 32 in steps S217d or S217e.

An additional feature of the present invention is recordation of addressee and sender information for suspect mailpieces and recordation of suspect criteria for which the mailpiece was determined to be suspect. A video image of the mailpiece can also be stored with the suspect information. Such information can be used by law enforcement personnel to attempt to determine the origin of the mailpieces. Additional information such as the time and date of sort or receipt, recipient information and sender information, cancellation zip code can also be stored. Such information could later be used as additional suspect criteria. Additionally, the system 153 could be connected to, for example, the USPS, a private investigator or law enforcement agencies so that information such as a video image of the suspect mailpiece 30a or data obtained from the mailpiece could be transmitted to such investigation entity 28 and possibly stored in a database 28a belonging to the investigation entity 28.

The present invention provides a system and method for helping to deter delays in the mail delivery. Another additional advantage of the present invention is that the negative impact of delayed mail delivery is reduced. It further provides the ability to protect recipients receipt of life threatening mailpieces. While the present invention has been disclosed and described with reference to a single embodiment thereof, it will be apparent, as noted above that variations and modifications may be made therein. It is, thus, intended in the following claims to cover each variation and modification that falls within the true spirit and scope of the present invention.

What is claimed is:

1. A system for sorting mailpieces and determining whether a mailpiece is suspected of containing harmful material, the system comprising comprising:

a component for singulating and feeding a mailpiece along a feed path of the system;

a system for reading the mailpiece, the system for reading the mailpiece positioned downstream from the component for singulating and feeding the mailpiece along the feed path;

a control system for controlling the system for sorting mailpieces and determining whether the mailpiece is suspected of containing harmful material or is a trusted, mailpiece;

a printer for printing an identification code on the mailpiece if the mailpiece is determined to be suspect;

a diverter for diverting the mailpiece into a collection module if the mailpiece is determined to be suspect; and a bin module comprising two or more destination bins for receiving the mailpiece if the mailpiece has been determined to be trusted.

2. The system as claimed in claim 1 wherein the system for reading the mailpiece includes an optical scanner which comprises a light source, a lens and sensor, the optical scanner senses a tape area on the mailpiece by detecting an optical difference between the tape area and the non-tape area.

3. A system for sorting mailpieces and determining whether a mailpiece is suspected of containing harmful material, the system comprising comprising:

a component for singulating and feeding a mailpiece along a feed path of the system;

a system for reading the mailpiece, the system for reading the mailpiece positioned downstream from the component for singulating and feeding the mailpiece along the feed path; and a control system for controlling the system for sorting mailpieces and determining whether the mailpiece is suspected of containing harmful material or is a trusted, mailpiece, wherein the control system provides processing of information read from the mailpiece by comparison of the information read from the mailpiece to information in an addressee database and information in a suspect database, the comparison to the suspect database for determining whether the mailpiece is suspected of containing harmful material and the comparison to the addressee database is for determining the appropriate addressee and destination bin for a trusted mailpiece.

4. A system for sorting mailpieces and determining whether a mailpiece is suspected of containing harmful material, the system comprising comprising:

a component for singulating and feeding a mailpiece along a feed path of the system;

a system for reading the mailpiece, the system for reading the mailpiece positioned downstream from the component for singulating and feeding the mailpiece along the feed path; and a control system for controlling the system for sorting mailpieces and determining whether the mailpiece is suspected of containing harmful material or is a trusted, mailpiece, further comprising a video coding terminal coupled to the system for sorting mailpieces and determining whether the mailpiece is suspected of containing harmful material, the video coding terminal for receiving a video image of the suspect mailpiece, the video image obtained from the system for reading the mailpiece, the video coding terminal for use by an operator to make a final determination as to the suspect status of the mailpiece.

5. The system as claimed in claim 4 therein the video coding terminal is located remotely from the system.

6. A system for sorting mailpieces and determining whether a mailpiece is suspected of containing harmful material, the system comprising comprising:

a component for singulating and feeding a mailpiece alone a feed path of the system;

a system for reading the mailpiece, the system for reading the mailpiece positioned downstream from the component for singulating and feeding the mailpiece alone the feed path; and a control system for controlling the system for sorting mailpieces and determining whether the mailpiece is suspected of containing harmful material or is a trusted, mailpiece, further comprising a web server coupled to the system for a sorting mailpieces and determining whether the mailpiece is suspected of containing harmful material, the web server for connecting the system for sorting mailpieces and determining whether the mailpiece is suspected of containing harmful material to an investigation entity and for facilitating sending of the video image of the suspect mailpiece and information from the suspect mailpiece to the investigation entity.

7. The system as claimed in claim 6 further comprising a profile database, connected to the investigation entity the profile database for storing video images of the suspect mailpiece and information from the suspect mailpiece.

8. A system for sorting mailpieces and determining whether a mailpiece is suspected of containing harmful material, the system comprising comprising:

a component for singulating and feeding a mailpiece along a feed path of the system;

a system for reading the mailpiece, the system for reading the mailpiece positioned downstream from the component for singulating and feeding the mailpiece along the feed path; and a control system for controlling the system for sorting mailpieces and determining whether the mailpiece is suspected of containing harmful material or is a trusted, mailpiece;

a detection area, the detection area containing the component for singulating and feeding a mailpiece, the system for reading the mailpiece, the control system, the diverter and the collection module; and a clean area, the clean area for containing the bin module, the clean area connected to the detection area at a transition area, the detection area having an area pressure lesser than an air pressure in the clean area whereby air flow is from the clean area to the detection area.

9. The system as claimed in claim 8 wherein the detection area further comprises a printer for printing an identification code on the mailpiece.

10. The system as claimed in claim 8 further comprising:

a video coding terminal coupled to the system for sorting mailpieces and determining whether the mailpiece is suspected of containing harmful material, the video coding terminal for receiving a video image of the suspect mailpiece, the video image obtained from the system for reading the mailpiece, the video coding terminal for use by an operator to make a final determination as to the suspect status of the mailpiece; and wherein the clean area further comprises a video coding terminal for observing a video image of the mailpiece.

11. A method of sorting mailpieces and determining whether a mailpiece is suspected of containing harmful materials using a mailpiece processing system, the method comprising the steps of:

a. singulating and feeding a mailpiece along a feed path of the system;

b. reading the mailpiece as the mailpiece moves along the feed path to obtain information about the mailpiece;

c. determining whether the mailpiece is suspected of containing harmful material or is a trusted, mailpiece based upon the information read from the mailpiece;

d. printing an identification code on the mailpiece if the mailpiece is determined to be suspect; and e. diverting the mailpiece into a collection module if the mailpiece is determined to be suspect.

12. A method of sorting mailpieces and determining whether a mailpiece is suspected of containing harmful materials using a mailpiece processing system, the method comprising the steps of:

a. singulating and feeding a mailpiece along a feed path of the system;

b. reading the mailpiece as the mailpiece moves along the feed path to obtain information about the mailpiece;

c. determining whether the mailpiece is suspected of containing harmful material or is a trusted, mailpiece based upon the information read from the mailpiece;

d. processing the information read from the mailpiece by comparison of the information read from the mailpiece to information in an addressee database and information in a suspect database, the comparison to the suspect database for determining whether the mailpiece is suspected of containing harmful material and the comparison to the addressee database is for determining the appropriate addressee and destination bin for a trusted mailpiece.

13. A method of sorting mailpieces and determining whether a mailpiece is suspected of containing harmful materials using a mailpiece processing system, the method comprising the steps of:
   a. singulating and feeding a mailpiece along a feed path of the system;
   b. reading the mailpiece as the mailpiece moves along the feed path to obtain information about the mailpiece;
   c. determining whether the mailpiece is suspected of containing harmful material or is a trusted, mailpiece based upon the information read from the mailpiece;
   d. receiving a video image of the suspect mailpiece at a video coding the video coding terminal for use by an operator to make a final determination as to the suspect status of the mailpiece.

14. The method as claimed in claim 13 further comprising the steps of:
   e. sending of the video image of the suspect mailpiece and information from the suspect mailpiece to an investigation entity.

15. The method as claimed in claim 13 further comprising the steps of:
   e. storing the video image of the suspect mailpiece and information from the suspect mailpiece in a profile database an the investigation entity.

16. The method as claimed in claim 15 wherein the information from the suspect mailpiece comprises a time and date of sort, a date and time of receipt, recipient information, sender Information, and cancellation zip code.

17. A method of sorting mailpieces and determining whether a mailpiece is suspected of containing harmful materials using a mailpiece processing system, the method comprising the steps of:
   a. singulating and feeding a mailpiece along a feed path of the system;
   b. reading the mailpiece as the mailpiece moves along the feed path to obtain information about the mailpiece;
   c. determining whether the mailpiece is suspected of containing harmful material or is a trusted, mailpiece based upon the information read from the mailpiece, the determination made by comparison of the information read from the mailpiece to information in an addressee database and information in a suspect database, the comparison to the suspect database for determining whether the mailpiece is suspected of containing harmful material and the comparison to the addressee database is for determining the appropriate addressee and destination bin for a trusted mailpiece;
   d. printing an identification code on the mailpiece if the mailpiece is determined to be suspect;
   e. diverting the mailpiece into a collection module if the mailpiece is determined to be suspect;
   f. receiving the mailpiece in a bin module if the mailpiece has been determined to be trusted;
   g. receiving a video image of the suspect mailpiece at a video coding the video coding terminal for use by an operator to make a final determination as to the suspect status of the mailpiece;
   h. sending of the video image of the suspect mailpiece and information from the suspect mailpiece to an investigation entity; and
   i. storing the video image of the suspect mailpiece and information from the suspect mailpiece in a profile database an the investigation entity;
   whereby the determination as to whether the mailpiece is suspect or trusted includes determining whether the mailpiece contains a predetermined amount of suspect criteria; and
   wherein the information from the suspect mailpiece comprises a time and date of sort, a date and time of receipt, recipient information, sender information, and cancellation zip code.

* * * * *